United States Patent [19]
Bertolotti et al.

[11] Patent Number: 5,797,749
[45] Date of Patent: Aug. 25, 1998

[54] DENTAL COMPOSITION

[75] Inventors: Raymond L. Bertolotti, Oakland; Thomas S. Blake, Danville, both of Calif.

[73] Assignee: Danville Materials, San Ramon, Calif.

[21] Appl. No.: 820,567

[22] Filed: Mar. 19, 1997

[51] Int. Cl.⁶ .................................................. A61C 5/00

[52] U.S. Cl. ................... 433/228.1; 433/226; 433/217.1

[58] Field of Search .................................. 433/215, 216, 433/217.1, 222.1, 226, 228.1

[56] References Cited

U.S. PATENT DOCUMENTS

| | | |
|---|---|---|
| 4,593,054 | 6/1986 | Asmussen et al. |
| 4,795,761 | 1/1989 | Curtis-Prior et al. .................. 514/652 |
| 4,999,386 | 3/1991 | Oakes et al. ............................ 523/122 |
| 5,154,920 | 10/1992 | Flesher et al. .......................... 514/643 |

*Primary Examiner*—Nicholas D. Lucchesi
*Attorney, Agent, or Firm*—Cooley Goodward LLP

[57] ABSTRACT

An aqueous-based dental composition useful for desensitizing an exposed tooth surface in preparation for performing restorative work on the tooth surface. The composition comprises benzethonium chloride, 2-hydroxyethyl methacrylate, water and optionally a small amount of a fluoride salt. The composition is used in the method of repairing a damaged tooth.

20 Claims, No Drawings

5,797,749

1

DENTAL COMPOSITION

FIELD OF THE INVENTION

This invention relates to a composition that is useful as a desensitizing agent which can be placed under dental cement and temporary provisional or final restorative dental materials to reduce post-operative sensitivity. The composition comprises an aqueous mixture of benzethonium chloride and 2-hydroxyethyl methacrylate (HEMA).

BACKGROUND OF THE INVENTION

In the process of repairing teeth it is often useful for a dentist to provide a temporary or provisional material to a tooth surface before providing the final restorative material. In that process it is generally a standard procedure to apply a desensitizing or bond enhancing agent to the prepared tooth surface, which generally has dentin exposed, before further restorative work is done. Applying such material provides relief from pain due to hypersensitivity of the patient's nerve ending and aids in the elimination of residual infection. It is thought that this material helps fill tubules and this helps in the pain relief aspects. A number of products are available for this purpose but many of them have glutaraldehyde as one of their primary components. Glutaraldehyde causes irritation in certain patients. It would be desirable to have a composition that could be used that would minimize such irritation while still giving the same or better results for the dentist.

It is now then discovered that a particular combination of benzethonium chloride and HEMA provides an improved combination that stops sensitivity in most people without irritating the surrounding soft tissue.

SUMMARY OF THE INVENTION

One aspect of this invention is an aqueous-based dental composition comprising about 0.25% by weight to about 20% by weight benzethonium chloride, about 10% by weight to about 60% by weight 2-hydroxyethyl methacrylate, and the remainder water.

Another aspect of this invention is a method of repairing a damaged tooth.

The method comprises (a) applying the above composition to a cleaned surface of the tooth having exposed dentin, (b) allowing the composition to permeate the surface of the exposed dentin, (c) optionally allowing the applied composition to at least partially dry, and (d) placing a restorative material on the surface of the exposed dentin to repair the tooth.

A further aspect of this invention is a method for preparing an aqueous-based dental composition that comprises mixing benzethonium chloride with 2-hydroxyethyl methacrylate in water to form a composition comprising about 0.25% by weight to about 20% by weight benzethonium chloride, about 10% by weight to about 60% by weight 2-hydroxyethyl methacrylate, and the remainder water.

Still another aspect of this invention is a method of repairing a damaged tooth which comprises (a) acid etching a cleaned surface of the tooth having exposed dentin, (b) applying the above composition to the acid-etched surface, (c) allowing the composition to permeate the surface of the exposed dentin,

2

(d) optionally allowing the applied composition to at least partially dry, (e) applying a composite binding agent to the exposed surface, and (f) binding a restorative material on the surface of the exposed surface to repair the tooth.

DETAILED DESCRIPTION AND PRESENTLY PREFERRED EMBODIMENTS

The Composition

One aspect of this invention is a dental composition useful for desensitizing a patient's tooth. The composition is used by a dentist in the process of repairing a damaged tooth and comprises benzethonium chloride, 2-hydroxyethyl methacrylate and water. In general, desensitizing compositions comprise an antibacterial in combination with a material that reduces the pain, i.e., tooth sensitivity due to exposed dentin, involved in the process of tooth repair. Broadly, the composition is an aqueous-based solution that comprises between about 0.25% by weight to 20% by weight of the benzethonium chloride with about 10% weight to about 60% by weight of the HEMA with the remainder being water. In addition, the composition may also include up to 100 parts per million of sodium fluoride. Preferably the benzethonium chloride will be present in an amount equal to about 1% by weight to about 10% by weight, with the HEMA present in an amount equal to about 20% by weight to about 50% by weight and the sodium fluoride being present in an amount equal to about 10 parts per million (PPM) and water making up the balance of the composition. Benzethonium chloride is defined in the "Merck Index Eleventh Edition" as N,N-Dimethyl-N-[2-[2-[4-(1,1,3,3-tetramethylbutyl)phenoxy]ethoxy]ethyl]benzenemethanaminium chloride.

To prepare the composition of this invention the ingredients are mixed in a suitable mixing apparatus to form a uniform mixture or solution. Because HEMA polymerizes more readily in the absence of oxygen and at elevated temperatures, the mixing is preferably done in the presence of oxygen. Usually this is done by aerating the mixture by bubbling air through the aqueous mixture during the preparation process. The mixing may be done on a batch basis or in a continuing process. Once a batch of the composition is prepared, it may be packaged in smaller containers to be distributed to dentists for final use.

Method of Repairing Teeth

Dental caries (tooth decay) is one of the most prevalent diseases affecting humans, and the greatest portion of a dentist's time and effort is expended on treating dental decay and its consequences. In addition to caries, teeth can be damaged by trauma, erosion, abrasion and other means. Restorative dentistry encompasses efforts to conserve and restore decayed, defective and traumatically injured teeth. In the process of repairing a damaged tooth, the dentist generally uses a number of pieces of equipment to permit the rapid removal of tooth structure to provide a surface which can be cleaned and ultimately treated in a manner to restore the tooth to a useful condition. In general, the dentist must prepare the tooth surface so that a proper restoration can be made and the damaged tooth can be repaired. In preparing a surface for further restoration work, the enamel, which is the hardest tissue in the body and which has no nerve supply, often must be abraded away to provide a surface which is then restored to a useful condition. In the process of abrading away the enamel, the dentin, which is a very bone-like structure and which makes up the bulk of the tooth, is exposed. A rich nerve supply makes dentin a highly sensitive tissue. The composition of this invention is useful in desensitizing the nerve endings and thus providing a lower sensation of pain to the patient undergoing repair of the damaged tooth. The composition also provides improved binding characteristics of the dentin surface. The composition of this invention is used in instances where the restorative material is retained by undercutting the tooth and using an amalgam or something similar to retain the tooth in position as well as using it in a situation where bonding to the dentin surface is required. In general, the method of repairing a damaged tooth in accordance with the invention comprises a series of steps. These are (a) applying a composition of this invention to a clean surface of the tooth having exposed dentin, (b) allowing the composition to permeate the surface of the exposed dentin, (c) optionally allowing the applied composition to at least partially dry, and (d) placing a restorative material on the surface of the exposed dentin to repair the tooth.

In general, in preparing the surface of the tooth having the exposed dentin, it is first cleaned before further work is done on the tooth. Generally the cleaning will involve preparation of the tooth surface using an appropriate drill or scraping tool. This can be done with any of the standard rotary drilling instruments having heads fashioned from diamonds or ultra hard steel or using micro-etching air abrasive means to prepare the surface and get it cleaned for an appropriate bond or other restoration. The surface is washed with water and dried to a certain extent, although complete dryness is not necessary before the application of the composition of this invention to the surface. Once the composition is applied to the surface it is allowed to permeate the surface of the exposed dentin. This generally takes place in a matter of a few seconds, less than a minute, to permeate the dentin. It is believed that the HEMA polymerizes closing the dental tubules, thus shutting down the transmission of nerve impulses in the tubules. Once the composition has sufficiently permeated the surface of the exposed dentin the composition optionally may be dried if the further step of placing the restorative material on the surface requires such drying. Finally, a restorative material is placed on the surface of the exposed dentin to repair the tooth. As mentioned, the restorative material may be an amalgam or may be material that is bound by a composite binding material.

If the restorative material is to be bound onto the exposed surface of the tooth, the clean surface of the tooth is first acid etched to ensure a proper binding to the surface will take place. Generally, the acid etching is done with phosphoric acid in about 10% to about 40% strength. Usually a small amount of the acid is placed on the surface for 15 to 30 seconds and is thoroughly rinsed then dried with air as required, although drying is not critical. Once the clean surface of the tooth is acid etched, the composition of this invention is applied to the surface allowing the composition to permeate the surface of the exposed dentin. Optionally, the composition is at least partially dried and a composite binding agent is applied to the exposed surface. Finally, the restorative material is placed on the exposed surface, having the binding agent and is bound to the surface to thus repair the tooth.

All publications and patent applications mentioned in this specification are herein incorporated by reference to the same extent as if each individual publication or patent application was specifically and individually indicated to be incorporated by reference.

The following examples set forth specific, non-limiting representations of the various aspects of this invention.

EXAMPLES

Example I. This example sets forth a specific composition useful for desensitizing a dentin surface that is exposed during the tooth repair process. Sufficient amounts of benzethonium chloride, 2-hydroxyethyl methacrylate (HEMA) sodium fluoride and water are thoroughly mixed to give a composition that has the following composition:

| benzethonium chloride | 2% by wt. |
|---|---|
| HEMA | 35% by wt. |
| Purified water USP | 63% by wt. |
| sodium fluoride | 10 ppm |

Example II. This example sets forth a method in which the composition of the invention is used for a nonbonding application. The following steps are used in a process of this invention.

1. The tooth prep area that will be treated is cleaned using standard dental techniques in the art.
2. Once the prep area is clean it is dried with air (although absolute dryness is not critical).
3. The composition of Example I is applied to the tooth using a brush or cotton pellet. At this point one should avoid contacting soft tissue although this is not as important as with some other compositions because the composition of this invention is significantly less irritating than those known in the art.
4. Once the composition is applied it is allowed to dry in the mouth for up to a minute (generally about 30 seconds) and then is dried with air.
5. Thereafter the restorative material which is to be placed on the prepared tooth area such as amalgam, castings, etc. is placed on the area. In this regard zinc phosphate and glass ionomer cements work particularly well with the composition of this invention.

Example III. This example sets forth a method for using the composition of this invention for a bonding application. In this application the following steps are generally performed:

1. The tooth prep area is cleaned.
2. The cleaned area is then etched with 10–40% phosphoric acid for up to a minute generally not more than 15 to 30 seconds.
3. The area is rinsed with water.
4. The rinsed area is then dried with air, although drying is not critical.
5. The composition of Example I is applied to the surface using a brush or cotton pellet.
6. About 60 seconds is then allowed to pass generally not more than 30 seconds then the surface is dried.
7. For direct restoration, the composite bonding agent and the composite material are applied in accordance with the manufacturer's instructions. For indirect restoration or sealing preparations, the composite binding agent and luting resin is applied in accordance with the manufacturer's instructions.

The invention now being fully described, it will be apparent to one of ordinary skill in the art that many changes and modifications can be made thereto without departing from the spirit or scope of the appended claims.

What is claimed is:

1. An aqueous-based dental composition comprising about 0.25% by weight to about 20% by weight benzethonium chloride, about 10% by weight to about 60% by weight 2-hydroxyethyl methacrylate, and the remainder water.

2. The composition of claim 1 comprising about 1% by weight to about 10% by weight benzethonium chloride, about 20% by weight to about 50% by weight 2-hydroxyethyl methacrylate, and the remainder water.

3. The composition of claim 2 comprising about 2% by weight benzethonium chloride, about 35% by weight 2-hydroxyethyl methacrylate, and the remainder water.

4. The composition of claim 3 with about 10 parts per million (ppm) sodium fluoride.

5. The composition of claim 1 with about 1 ppm to about 100 ppm fluoride salt.

6. A method of repairing a damaged tooth which comprises (a) applying a composition of claim 1 to a cleaned surface of the tooth having exposed dentin, (b) allowing the composition to permeate the surface of the exposed dentin, (c) optionally allowing the applied composition to at least partially dry, and (d) placing a restorative material on the surface of the exposed dentin to repair the tooth.

7. The method of claim 6 wherein the composition comprises about 1% by weight to about 10% by weight benzethonium chloride, about 20% by weight to about 50% by weight 2-hydroxyethyl methacrylate, and the remainder water.

8. The method of claim 7 wherein the composition comprises about 2% by weight benzethonium chloride, about 35% by weight 2-hydroxyethyl methacrylate, and the remainder water.

9. The method of claim 8 wherein the composition comprises in addition about 10 parts per million (ppm) sodium fluoride.

10. The method of claim 6 wherein the composition comprises in addition about 1 ppm to about 100 ppm fluoride salt.

11. A method of repairing a damaged tooth, which method comprises (a) acid etching a cleaned surface of the tooth having exposed dentin, (b) applying a composition of claim 1 to the acid-etched surface, (c) allowing the composition to permeate the surface of the exposed dentin, (d) optionally allowing the applied composition to at least partially dry, (e) applying a composite binding agent to the exposed surface, and (f) binding a restorative material on the surface of the exposed surface to repair the tooth.

12. The method of claim 11 wherein the composition comprises about 1% by weight to about 10% by weight benzethonium chloride, about 20% by weight to about 50% by weight 2-hydroxyethyl methacrylate, and the remainder water.

13. The method of claim 12 wherein the composition comprises about 2% by weight benzethonium chloride, about 35% by weight 2-hydroxyethyl methacrylate, and the remainder water.

14. The method of claim 13 wherein the composition comprises in addition about 10 parts per million (ppm) sodium fluoride.

15. The method of claim 11 wherein the composition comprises in addition about 1 ppm to about 100 ppm fluoride salt.

16. A method for preparing an aqueous-based dental composition that comprises mixing benzethonium chloride with 2-hydroxyethyl methacrylate in water to form a composition comprising about 0.25% by weight to about 20% by weight benzethonium chloride, about 10% by weight to about 60% by weight 2-hydroxyethyl methacrylate, and the remainder water.

17. The method of claim 16 wherein the composition comprises about 1% by weight to about 10% by weight benzethonium chloride, about 20% by weight to about 50% by weight 2-hydroxyethyl methacrylate, and the remainder water.

18. The method of claim 17 wherein the composition comprises about 2% by weight benzethonium chloride, about 35% by weight 2-hydroxyethyl methacrylate, and the remainder water.

19. The method of claim 18 wherein the composition comprises in addition about 10 parts per million (ppm) sodium fluoride.

20. The method of claim 16 wherein the composition comprises in addition about 1 ppm to about 100 ppm fluoride salt.

* * * * *